(12) United States Patent
O'Brien et al.

(10) Patent No.: US 7,687,677 B1
(45) Date of Patent: Mar. 30, 2010

(54) PROCESS FOR RECOVERING THERMAL ENERGY FROM A REACTOR EFFLUENT STREAM

(75) Inventors: Dennis E. O'Brien, Arlington Heights, IL (US); Joseph E. Zimmermann, Arlington Heights, IL (US); Douglas G. Stewart, Wheeling, IL (US)

(73) Assignee: UOP LLC, Des Plaines, IL (US)

( * ) Notice: Subject to any disclaimer, the term of this patent is extended or adjusted under 35 U.S.C. 154(b) by 781 days.

(21) Appl. No.: 11/541,157

(22) Filed: Sep. 29, 2006

(51) Int. Cl.
*C07C 7/11* (2006.01)

(52) U.S. Cl. .................. 585/809; 585/634; 585/639; 585/654; 585/655; 585/658; 585/804; 585/807; 585/867; 585/910

(58) Field of Classification Search .............. 585/634, 585/639, 654, 655, 658, 809, 910, 867, 807, 585/804
See application file for complete search history.

(56) References Cited

U.S. PATENT DOCUMENTS

| | | | |
|---|---|---|---|
| 5,214,225 A | * | 5/1993 | Hall et al. .................. 585/654 |
| 5,345,025 A | | 9/1994 | Mitariten et al. |
| 5,849,979 A | * | 12/1998 | Kalnes et al. ................ 585/809 |
| 6,403,854 B1 | | 6/2002 | Miller et al. |
| 6,417,420 B1 | | 7/2002 | Stewart et al. |
| 6,459,009 B1 | | 10/2002 | Miller et al. |
| 6,479,720 B1 | | 11/2002 | O'Brien et al. |
| 6,762,334 B1 | | 7/2004 | Stewart et al. |
| 7,011,740 B2 | | 3/2006 | Tallman et al. |
| 7,038,102 B2 | | 5/2006 | Van Egmond et al. |

* cited by examiner

*Primary Examiner*—In Suk Bullock
*Assistant Examiner*—Prem C. Singh
(74) *Attorney, Agent, or Firm*—Arthur E. Gooding (57) ABSTRACT

A processing scheme and arrangement for enhanced olefin production involves recovering thermal energy from a reactor effluent stream resulting from the dehydrogenation of a dehydrogenatable hydrocarbon. The process involves contacting the reactor effluent stream with a circulating fluid stream in a first contact cooling zone to produce a product stream and to form a heated circulating fluid stream. Thermal energy is recovered from the heated circulating fluid stream via indirect heat exchange with a first process stream in a first heat exchange zone to form a cooled circulating fluid stream. The cooled circulating fluid stream can be subsequently cooled and at least a first portion thereof returned to the first contact cooling zone.

19 Claims, 2 Drawing Sheets

PROCESS FOR RECOVERING THERMAL ENERGY FROM A REACTOR EFFLUENT STREAM

FIELD OF THE INVENTION

This invention relates generally to hydrocarbon processing and, more particularly, to recovering thermal energy from catalytic dehydrogenation effluent streams to enhance olefin production.

BACKGROUND OF THE INVENTION

Olefinic hydrocarbons such as, for example, propylene and butylene, are one of the major building blocks of a large number of petrochemical products. Such olefinic hydrocarbons are also useful in petroleum refineries for the production of motor fuel blending components. In view of the commercial desirability of such olefinic hydrocarbons, there is a continuing search for techniques to lower the cost of production and increase the relative yield of such olefins.

One process for producing olefins such as, for example, propylene, involves the catalytic dehydrogenation of a dehydrogenatable hydrocarbon-containing feedstock such as, for example, a propane-containing feedstock. Such catalytic dehydrogenation processes generally involve mixing the dehydrogenatable hydrocarbon-containing feedstock with a hydrogen-rich gas stream and introducing the combined feedstock into a reactor section, typically including several reactor units connected in series, wherein at least a portion of the dehydrogenatable hydrocarbons in the combined feedstock are catalytically converted to produce a reactor effluent stream containing at least a corresponding olefin product. Generally, such dehydrogenation reactor effluent streams have a temperature in excess of about 150° C. (about 300° F.).

Such dehydrogenation reactor effluent streams are subsequently cooled and compressed to facilitate separation into individual product streams. Dehydrogenation reactor effluent streams can be cooled using various heat exchange methods such as, for example, indirect heat exchange with a cooling medium such as, for example, cooling water. One such indirect heat exchange method generally involves passing the hot dehydrogenation reactor effluent stream through a heat exchange unit such as, for example, a tube and sheet heat exchanger, to produce a cooled effluent stream having a temperature profile that is suitable for efficient compression.

However, such indirect heat exchange units can be susceptible to fouling by constituents of the dehydrogenation reactor effluent stream. For example, heavy hydrocarbon compounds (i.e., $C_7+$ hydrocarbons) contained in the dehydrogenation reactor effluent stream can condense on surfaces of the heat exchange unit which can result in a reduction of the cooling capacity of the heat exchange unit. Generally, the temperature of a gas to be compressed determines, at least in part, the capacity of an associated compressor, i.e., the higher the temperature of the gas the less it can be compressed. Thus, reducing the cooling capacity of the heat exchange unit results in a reduced compression capacity in an associated compressor which can, in turn, result in increased down time for cleaning of the heat exchange units and decreased product output.

In view of the above, there is a need and a demand for processing schemes and/or arrangements effective to reduce fouling of heat exchange units used to cool dehydrogenation reactor effluent streams.

Additionally, gaseous materials which pass through such indirect heat exchange units can also experience a significant pressure drop from inlet to outlet resulting in a cooled product stream being at a pressure which is lower than may be desired and can require additional energy expenditures to compress the cooled product stream to a pressure suitable for further processing in subsequent separation units. Thus, there is a further need and a demand for processing schemes and/or arrangements that result in reduced pressure drop across the heat exchange unit.

Further, a pressure drop across the heat exchange unit can result in an increased pressure at an associated dehydrogenation section outlet which can cause reductions in the yield of olefins, such as propylene, produced by the dehydrogenation process. Accordingly, there is a still further need and a demand for processing schemes and/or arrangements effective to result in an increased relative yield of olefins, particularly, propylene.

SUMMARY OF THE INVENTION

A general objective of the invention is to provide an improved process and system for producing olefins via catalytic dehydrogenation of dehydrogenatable hydrocarbons.

A more specific objective of the invention is to overcome one or more of the problems described above.

The general object of the invention can be attained, at least in part, through a process for recovering thermal energy from a reactor effluent stream resulting from dehydrogenation of a dehydrogenatable hydrocarbon. Such process involves contacting the reactor effluent stream with a circulating fluid stream in a first contact cooling zone wherein the reactor effluent stream is cooled to form a first product stream and the circulating fluid stream is heated to form a first heated circulating fluid stream. Thermal energy is subsequently recovered from the first heated circulating fluid stream via indirect heat exchange with a first process stream in a first heat exchange zone wherein the first heated circulating fluid stream is cooled to form a first cooled circulating fluid stream and the first process stream is heated to form a first heated process stream. The process can further involve cooling at least a portion of the first cooled circulating fluid stream to provide the circulating fluid stream and recycling the circulating fluid stream to contact cooling zone. The process can also involve compressing the first product stream in one or more compression zones and recovering thermal energy from the compressed product stream.

The prior art generally fails to provide processing schemes and arrangements that are as effective as desired in increasing the relative yield of olefins compared to conventional catalytic dehydrogenation and recovery processes. Further, the prior art generally fails to provide processing schemes and arrangements that result in desirably reduced fouling and/or pressure drop across associated heat exchange units. Additionally, the prior art generally fails to provide processing schemes and arrangements that are as effective as desired in recovering thermal energy from dehydrogenation reactor effluent streams and/or compressed product streams, and utilizing such recovered thermal energy to reduce external energy inputs typically required in conventional catalytic dehydrogenation and product recovery processes.

In accordance with another embodiment, a process for recovering thermal energy from a reactor effluent stream resulting from dehydrogenation of a dehydrogenatable hydrocarbon involves contacting the reactor effluent stream with a first circulating fluid stream in a first contact cooling zone wherein the reactor effluent stream is cooled to form a first product stream and the first circulating fluid stream is heated to form a first heated circulating fluid stream. The first product stream is compressed in a first compression zone to produce a first compressed product stream. The first compressed product stream subsequently contacts a second circulating fluid stream in a second contact cooling zone wherein the first compressed product stream is cooled to produce a second product stream and the second circulating fluid stream is heated to form a second heated circulating fluid stream. The first and second heated circulating fluid streams are combined to form a combined heated circulating fluid stream. The combined heated circulating stream is separated into a first drag stream and a heated recycle fluid stream. Thermal energy is recovered from the heated recycle fluid stream via indirect heat exchange with a first process stream in a first heat exchange zone wherein the heated recycle fluid stream is cooled to form a first cooled circulating fluid stream and the first process stream is heated to form a heated first process stream.

A system for recovering thermal energy from a reactor effluent stream resulting from dehydrogenation of a dehydrogenatable hydrocarbon is also provided. The system includes a first contact cooling zone wherein the reactor effluent stream contacts a circulating fluid stream to produce a product stream and to form a first heated circulating fluid stream. The system also includes a first heat exchange zone wherein thermal energy is recovered from the first heated circulating fluid stream via indirect heat exchange with a first process stream to form a first cooled circulating fluid stream and a first heated process stream. The system further includes a recycle loop including a second heat exchange zone wherein the first cooled circulating fluid stream is cooled via indirect heat exchange with at least a second process stream to provide the circulating fluid stream.

As used herein, references to a "dehydrogenatable hydrocarbon" are to be understood to generally refer to all classes of hydrocarbons containing saturated carbon bonds which have the potential for forming one or more unsaturated bonds through the process of dehydrogenation. The preferred dehydrogenatable hydrocarbons of the present invention consist of paraffin hydrocarbons. More specifically, the paraffin hydrocarbons may contain from 2 to about 30 carbon atoms. Representative members of this class include: ethane, propane, butane, isobutane, pentane, isopentane, hexane, heptane, nonane, decane, undecane, dodecane, tridecane, tetradecane, pentadecane, hexadecane, heptadecane, octadecane, and mixtures thereof. A particularly important class of paraffin hydrocarbons includes ethane, propane, butane, isobutane, pentane, isopentane and mixtures thereof which are readily prepared by the fractionation of relatively low boiling point hydrocarbon fractions.

Other objects and advantages will be apparent to those skilled in the art from the following detailed description taken in conjunction with the appended claims and drawings.

DETAILED DESCRIPTION OF THE INVENTION

A dehydrogenatable hydrocarbon feedstock can be converted in a dehydrogenation reactor unit to produce a reactor effluent stream containing a range of hydrocarbon products which can be subsequently recovered and/or recycled. In particular, in accordance with certain dehydrogenation processes, the selected dehydrogenatable hydrocarbon feedstock is introduced into a dehydrogenation zone containing a dehydrogenation catalyst and operating at dehydrogenation conditions wherein least a portion of the dehydrogenatable hydrocarbon feedstock is converted into an olefin-containing reactor effluent stream.

Such reactor effluent stream typically includes dehydrogenated hydrocarbons. i.e., light olefins, such as, for example, propylene; unconverted dehydrogenatable hydrocarbons such as, for example, propane; other light gas components such as, for example, ethane, ethylene, methane, hydrogen and mixtures thereof; and other hydrocarbons such as, for example, $C_4$ hydrocarbons and/or $C_4$ olefins such as, for example, butane and/or butylene, heavy hydrocarbons containing seven or more carbon atoms, and aromatic hydrocarbons such as, for example, benzene, toluene and/or xylene.

In accordance with certain embodiments further described below, the hydrocarbon feedstock includes at least one dehydrogenatable hydrocarbon selected from propane, butane, isobutene, isopentane, or combinations thereof. In accordance with certain further embodiments, the dehydrogenatable hydrocarbon feedstock can be a propane-containing feedstock.

Such dehydrogenation reactor units are generally operated at elevated temperatures and produce dehydrogenation reactor effluent streams having a temperature in a range of about 400° C. to about 900° C. (about 750° F. to about 1650° F.). Such dehydrogenation reactor effluent streams are typically initially cooled via indirect heat exchange with the dehydrogenatable hydrocarbon feedstock to provide a reactor effluent stream having a temperature in a range of about 120° C. to about 200° C. (about 250° F. to about 400° F.). The reactor effluent stream is generally subsequently further cooled and compressed to facilitate recovery of various product streams such as, for example, propylene streams, recyclable paraffin hydrocarbon streams containing ethane and/or propane, and hydrogen gas streams.

Figure 1:
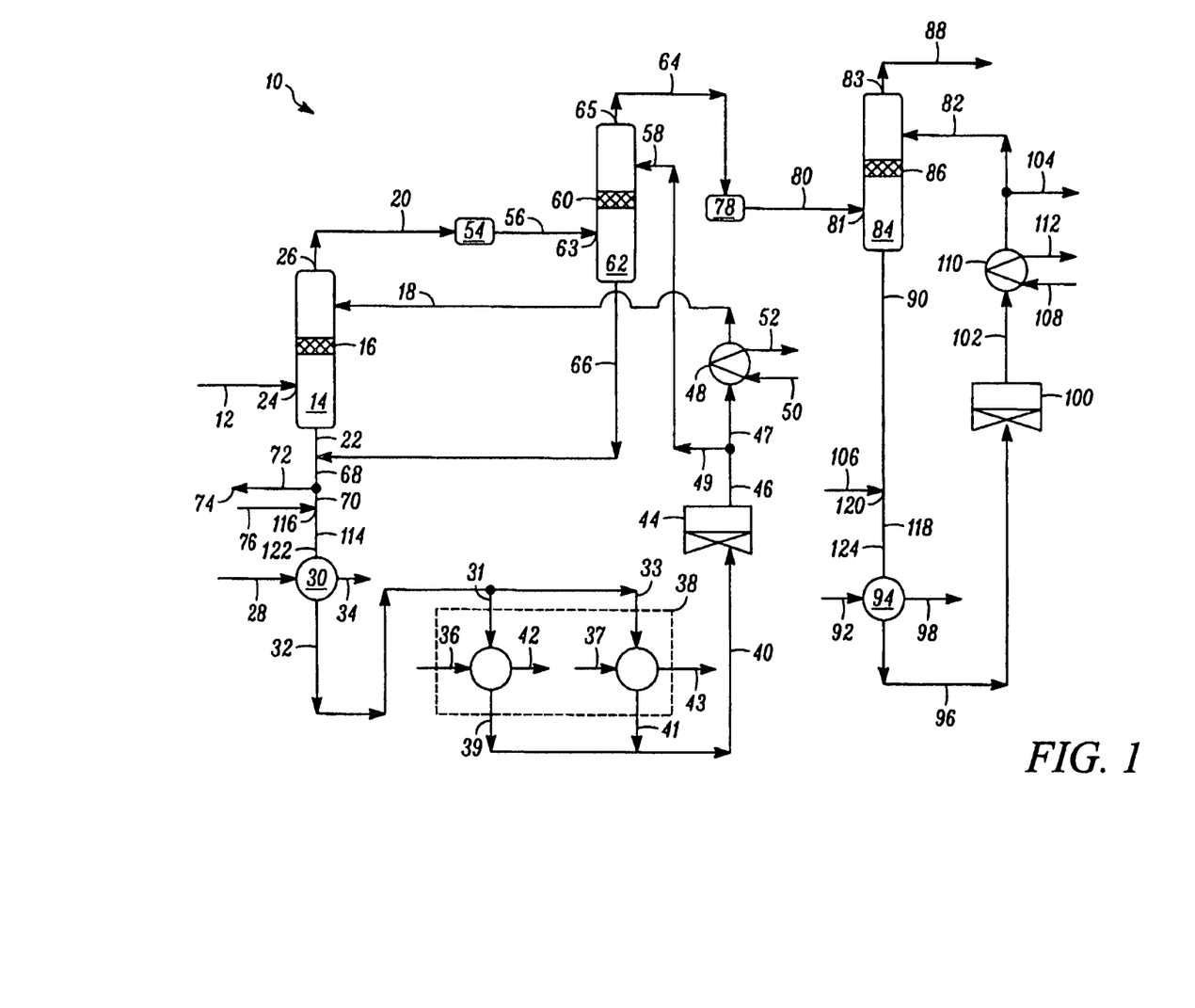
FIG. 1 is a simplified schematic diagram of a process for recovering thermal energy from a dehydrogenation reactor effluent stream in accordance with one embodiment.

FIG. 1 schematically illustrates a processing scheme and system, generally designated by the reference numeral 10, for recovering thermal energy from such reactor effluent stream 12 resulting from dehydrogenation of a dehydrogenatable hydrocarbon in accordance with one embodiment.

More particularly, in the processing scheme 10, the reactor effluent stream 12 is introduced into a first contact cooler 14 below a first contact cooling zone 16. A first circulating fluid stream 18 is introduced into the first contact cooler 14 above the first contact cooling zone 16. The reactor effluent stream 12 contacts the first circulating fluid stream 18 in the first contact cooling zone 16 in a countercurrent manner. The reactor effluent stream 12 is cooled to produce a first product stream 20 and the first circulating fluid stream 18 is heated to form a first heated circulating fluid stream 22.

Advantageously, materials passing through the first contact cooler 14 from a reactor effluent stream inlet 24 to a first product stream outlet 26 have a pressure drop of less than about 3.5 kPa (about 0.5 psi). In particular, it has been discovered that reducing or eliminating the pressure drop across the first contact cooler 14 allows reactors within the dehydrogenation reactor unit to operate at lower pressure. Lower pressures in the reactors generally favor increased conversion of paraffin hydrocarbons to corresponding dehydrogenated hydrocarbons at the same operating temperatures, liquid hourly space velocities (i.e., ratios of hydrocarbon feed volume to catalyst volume in the reactor unit) and/or hydrogen to hydrocarbon ratios in reactor unit feed streams.

For example, in accordance with certain embodiments, a reduction in dehydrogenation reactor pressure of about 14 kPa (about 2 psi) can result in about a 1% increase in propane conversion and about a 0.6% increase in propylene production at a fixed fresh propane feed rate.

Additionally, it has been discovered that by increasing conversion of propane to propylene, the amount of recycle propane produced decreases such that, for an existing unit, additional capacity in the dehydrogenation reactor section can be realized. For example, in a 350 kilometric ton per annum (KMTA) propylene-producing dehydrogenation reactor unit, reducing reactor pressure by about 14 kPa (about 2 psi) can result in about a 2.1 KMTA increase in propylene production.

In accordance with certain embodiments, the reactor effluent stream 12 may have a temperature in a range of 120° C. to about 200° C. (about 250° F. to about 400° F.) and may be cooled via contact with the first circulating fluid stream 18 in the first contact cooling zone 16 to produce the first product stream 20 having a temperature in a range of about 35° C. to about 55° C. (about 95° F. to about 130° F.). In accordance with certain further embodiments, the reactor effluent stream 12 may have a temperature in a range of about 150° C. to about 180° C. (about 300° F. to about 350° F.) and may be cooled to via contact with the first circulating fluid stream 18 to produce the first product stream 20 having a temperature in a range of about 37° C. to about 50° C. (about 100° F. to about 120° F.).

In practice, the first circulating fluid stream 18 having a temperature in a range of about 20° C. to about 40° C. (about 70° F. to about 105° F.) can be heated in the first contact cooling zone 16 to form the first heated circulating stream 22 having a temperature in a range of about 95° C. to about 150° C. (about 200° F. to about 300° F.). In accordance with certain embodiments, the first circulating fluid stream 18 may be heated in the first contact cooling zone 16 to form the first heated circulating fluid stream 22 having a temperature in a range of about 120° C. to about 150° C. (about 250° F. to about 300° F.).

Suitably, the reactor effluent stream 12 may have a delivery pressure in a range of about 7 to about 14 kPa gauge (about 1 to about 2 psig). In accordance with certain embodiments, the reactor effluent stream 12 may have a delivery pressure in a range of about 7.6 to about 8.3 kPa gauge (about 1.1 to about 1.2 psig).

In accordance with certain embodiments, as illustrated in FIG. 1, the first contact cooler 14 can include a single contact cooling zone 16. Alternatively, the first contact cooler 14 can include two or more contact cooling zones such that materials introduced into the first contact cooler 14 from the reactor effluent stream 12 contact materials introduced into the first contact cooler 14 from the first circulating fluid stream 18 at multiple locations within the contact cooler 14 to ensure efficient and effective heat transfer and/or adsorption of heavy hydrocarbons from the relatively hot reactor effluent stream 12 to the relatively cool first circulating fluid stream 18.

In accordance with certain embodiments, the first contact cooler 14 can include one or more contact cooling zones 16 in the form of a packed bed containing an inert packing material. Various suitable packing materials such as are known in the art can be employed in the packed bed. For example, the packed bed can contain a structured or random metal-type packing such as can be used in low pressure drop fractionation applications. In accordance with certain other embodiments, the contact cooler 14 may additionally or alternatively include one or more contact cooling zones 16 in the form of a tray assembly such as, for example, a disk and doughnut tray assembly or a side-to-side pan assembly.

Advantageously, the first circulating fluid stream 18 may absorb or otherwise extract heavy components such as, for example, $C_7+$ hydrocarbons and/or aromatic compounds such as, for example, benzene and toluene, from the reactor effluent stream 12 via physical contact of the reactor effluent stream 12 with the first circulating fluid stream 18 in the first contact cooling zone 16. Such heavy components are removed from the contact cooler 14 via the first heated circulating fluid stream 22.

In practice, it has been discovered that heavy hydrocarbons present in the reactor effluent stream 12 can cause fouling of conventional heat exchange units such as, for example, tube and sheet heat exchangers, associated with compressors used to facilitate fractionation of the first product stream 20 into select product fractions. When fouled, such conventional heat exchange units may not cool the product stream 20 as much as may be desired before the product stream is compressed. The associated compressor in turn can become capacity limited due to the higher temperature of the product stream and may require cleaning during a turn-around. In certain situations, it has been discovered fouling of such conventional heat exchange units can result in about a 1 to about 3 percent drop in capacity for an associated compressor. Thus, removal of heavy hydrocarbon components from the first product stream 20 prior to compression can result in improved operating economics by maintaining compressor capacities and reducing turn-around time.

The first circulating fluid stream 18 advantageously includes at least one $C_{10}+$ hydrocarbon material. The use of such $C_{10}+$ hydrocarbon materials is desirable to minimize and/or otherwise prevent vaporization of the circulating fluid material into the first product stream 20. In accordance with certain embodiments, the first circulating fluid stream 18 advantageously includes a material selected from light cycle oil, ultra-low sulfur diesel, kerosene and combinations thereof. In accordance with certain further embodiments, the first circulating fluid stream 18 advantageously includes ultra-low sulfur diesel.

Thermal energy is subsequently recovered from the first heated circulating fluid stream 22 via indirect heat exchange with a first process stream 28 in a first heat exchange zone 30. In practice, the first heated circulating fluid stream 22 is cooled via indirect heat exchange with the first process stream 28 to form a first cooled circulating fluid stream 32 and the first process stream 28 is heated via indirect heat exchange with the first heated circulating fluid stream 22 to form a first heated process stream 34.

In accordance with certain embodiments, the first heated circulating fluid stream 22 may be cooled to form the first cooled circulating fluid stream 32 having a temperature in a range of about 65° C. to about 95° C. (about 150° F. to about 200° F.) while the first process stream 28 having a temperature in a range of about 75° C. to about 100° C. (about 170° F. to about 210° F.) is heated to form the first heated process stream 34 having a temperature in a range of about 80° C. to about 105° C. (about 180° F. to about 220° F.).

In accordance with certain embodiments, the thermal energy recovered from the first heated circulating fluid stream 22 and transferred via indirect heat exchange into the first heated process stream 34 can be used to supplement and/or replace other sources of thermal energy such as, for example, steam, used in associated fractionation units. For example, the first heated process stream 34 may be introduced into an associated depropanizer unit (not shown) to facilitate fractionation of a propane-containing feed or byproduct stream, such as via a reboiling process, into a purified propane stream and a byproduct stream containing $C_4+$ hydrocarbons. In practice, such purified propane stream can be introduced or recycled into the dehydrogenation reactor unit.

For example, it has been discovered that thermal energy recovered from the first heated circulating fluid stream 22 can be used to supplant up to about 50% of steam that is generally required to reboil a separation column in an associated depropanizer unit. In accordance with certain embodiments, about 10 to about 40 MMBTU/hr of thermal energy may be recovered from the first heated circulating fluid stream 22 in the first heat exchange zone 30. In practice, for a 350 KMTA propylene-producing system, about 20-35 MMBTU/hr thermal energy recovered from the first heated circulating fluid stream 22 can be supplied to an associated depropanizer column reboiler.

It has further been discovered that the relief load of a separation column of an associated depropanizer unit can also be reduced by utilizing thermal energy recovered from the first heated circulating fluid stream 22 rather than steam for reboiling the column. In traditional systems using steam for column reboiling, the relief loads due to a general power failure, which assumes that heat input via steam continues to the column but heat removal via reflux pumps stops, is quite large. In contrast, in the present invention, in the event of a general power failure, pumps used to circulate the circulating fluid also stop. Thus, heat is no longer recovered from the heated circulating fluid and introduced into the column. As a result, the relief load on the separation column can be reduced.

In accordance with certain embodiments, at least a portion of the first cooled circulating fluid stream 32 can be subsequently further cooled and recycled to the first contact cooler 14 to provide the first circulating fluid stream 18.

For example, in accordance with certain embodiments, thermal energy can be recovered from the first cooled circulating fluid stream 32 via indirect heat exchange with at least one process stream 36 in an indirect heat exchange zone 38 to form a second cooled circulating fluid stream 40 and at least one heated process stream 42. In practice, the first cooled circulating fluid stream 32 can be cooled in the indirect heat exchange zone 38 to form the second cooled circulating fluid stream 40 having a temperature in a range of about 50° C. to about 65° C. (about 120° F. to about 150° F.). The at least one process stream 36 having a temperature in a range of about 30° C. to about 45° C. (about 85° F. to about 115° F.) can be heated in the indirect heat exchange zone 38 to form at least one heated process stream 42 having a temperature in a range of about 35° C. to about 50° C. (about 95° F. to about 120° F.). In accordance with certain further embodiments, about 10 to about 40 MMBTU/hr of thermal energy can be recovered from the first cooled circulating fluid stream 32 in the indirect heat exchange zone 38.

For example, as illustrated in FIG. 1, thermal energy is recovered from the first cooled circulating fluid stream 32 via indirect heat exchange with two process streams, fifth process stream 36 and sixth process stream 37, respectively. Thermal energy is recovered from a first portion 31 of the first cooled circulating fluid stream 32 via indirect heat exchange with the fifth process stream 36 to form a first portion 41 of the second cooled circulating fluid stream 40 and to produce a heated fifth process stream 42. Thermal energy is recovered from a second portion 33 of the first cooled circulating fluid stream 32 via indirect heat exchange with the sixth process stream 37 to form a second portion 41 of the second cooled circulating fluid stream 40 and to produce a heated sixth process stream 43. Suitably, the first and second portions, 39 and 41, respectively, are combined to form the second cooled circulating fluid stream 40. Alternatively, one of the first and second portions, 39 and 41, respectively, of the second cooled circulating fluid stream 40 can be drawn off such as in the form of a drag stream (not shown).

In practice, the at least one process stream 36 can be a dehydrogenatable hydrocarbon-containing stream containing a dehydrogenatable hydrocarbon selected from propane, butane, isobutene, isopentane and combinations thereof. In accordance with certain embodiments, the at least one dehydrogenatable hydrocarbon-containing stream 36 can be a propane-containing stream.

In accordance with further embodiments, the at least one dehydrogenatable hydrocarbon-containing stream 36 can be a fresh feed stream or a recycle feed stream. For example, in accordance with certain embodiments, the alpha process stream 36a or the beta process stream 36b can be a propane-containing fresh feed stream which is heated via indirect heat exchange with the first portion 32a of the first cooled circulating fluid stream 32 to provide a partially-vaporized propane-containing fresh feed stream 42a which can be introduced into a reboiler section of an associated depropanizer unit (not shown). Additionally or alternatively, the beta process stream 36b can be a propane-containing recycle feed stream such as, for example, a propane-containing recycle feed stream produced by an associated propane-propylene splitter unit (not shown), which is heated to provide a partially-vaporized propane-containing recycle stream 42b which can be introduced into a reboiler section of an associated depropanizer unit (not shown). Recovering thermal energy from the first cooled circulating fluid stream 32 and utilizing such recovered energy to partially vaporize propane-containing fresh and/or recycled feed streams can advantageously result in a reduced thermal energy demand in a reboiler section of an associated depropanizer unit thereby rendering the overall dehydrogenation process more economical to operate.

The second cooled circulating fluid stream 40 can be further cooled via indirect heat exchange in a second heat exchange zone 44 to form a third cooled circulating fluid stream 46. The second heat exchange zone 44 can include any suitable heat exchange unit such as known to those skilled in the art. In accordance with certain embodiments, the second heat exchange zone 44 can include an air cooler unit. In practice, the second cooled circulating fluid stream 40 can be cooled via indirect heat exchange in the second heat exchange zone 44 to form the third cooled circulating fluid stream 46 having a temperature in a range of about 35° C. to about 55° C. (about 95° F. to about 130° F.). In accordance with certain embodiments, the second cooled circulating fluid stream 40 can be cooled via indirect heat exchange in the second heat exchange zone 44 to form the third cooled circulating fluid stream 46 having a temperature in a range of about 40° C. to about 50° C. (about 105° F. to about 125° F.).

Thermal energy may be recovered from the third cooled circulating fluid stream 46 via indirect heat exchange in a third heat exchange zone 48 wherein the third cooled circulating fluid stream 46 is cooled to provide the first circulating fluid stream 18. In accordance with certain embodiments, thermal energy recovered from the third cooled circulating fluid stream 46 can be transferred to a third process stream 50 to produce a first treated process stream 52. Advantageously, thermal energy recovered from the third cooled circulating fluid stream 46 can be utilized to at least partially vaporize the components of the third process stream 50 which can then be introduced into an associated thermal processing unit such as, for example, a propane-propylene (P-P) splitter unit (not shown) in the form of the first treated process stream 52. In accordance with certain further embodiments, about 10 to about 40 MMBTU/hr of thermal energy can be recovered from the third cooled circulating fluid stream 46 and transferred to the first treated process stream 52 in the third heat exchange zone 48.

The processing scheme 10 can further involve compressing the first product stream 20 in a first compression zone 54 to produce a first compressed product stream 56 and contacting the first compressed product stream 56 with a second circulating fluid stream 58 in a second contact cooling zone 60 disposed within a second contact cooler 62. The first compressed product stream 56 contacts the second circulating fluid stream 58 in a countercurrent manner in the second contact cooling zone 60 wherein the first compressed product stream 56 is cooled to form a second product stream 64 and the second circulating fluid stream 58 is heated to form a second heated circulating fluid stream 66.

Similar to the first contact cooler 14, described herein above, the second contact cooler 62 can include one or more contact cooling zones 60 in the form of a packed bed containing an inert packing material and/or a tray assembly. Advantageously, materials passing through the second contact cooler 62 from a first compressed product stream inlet 63 to a second product stream outlet 65 have a pressure drop of less than about 3.5 kPa (about 0.5 psi).

In accordance with certain embodiments, the first product stream 20 is compressed in the first compression zone 54 to form the first compressed product stream 56 having a delivery pressure in a range of about 205 to about 275 kPa gauge (about 30 to about 40 prig) and having a temperature in a range of about 120° C. to about 150° C. (about 250° F. to about 300° F.). Suitably, the first compressed product stream 56 is cooled via contact with the second circulating fluid stream 58 in the second contact cooling zone 60 to form the second product stream 64 having a temperature in a range of about 35° C. to about 55° C. (about 95° F. to about 130° F.). Further, the second circulating fluid stream 58 having a temperature in a range of about 20° C. to about 40° C. (about 70° F. to about 105° F.) is heated via contact with the first compressed product stream 56 in the second contact cooling zone 60 to form the second heated circulating fluid stream 66 having a temperature in a range of about 65° C. to about 95° C. (about 150° F. to about 200° F.).

In accordance with certain further embodiments, a first portion 47 of the third cooled circulating fluid stream 46 may be recycled to provide the first circulating fluid stream 18 while a second portion 49 of the third cooled circulating fluid stream 46 may be recycled to provide the second circulating fluid stream 58.

The second heated circulating fluid stream 66 can be combined with the first heated circulating fluid stream 22 to form a combined heated circulating fluid stream 68 and at least a first portion 70 thereof can be cooled via indirect heat exchange in the first heat exchange zone 30.

In accordance with certain embodiments, a second portion 72 of the combined heated circulating fluid stream 68 can be removed from or drawn off the processing scheme 10 to produce a first drag stream 74. The first drag stream 74 is advantageously drawn off or removed from the processing scheme 10 to reduce or eliminate the build-up of heavy hydrocarbons such as, for example, $C_7$+ hydrocarbons especially $C_{12}$+ hydrocarbons, and/or aromatic hydrocarbons such as, for example, benzene and toluene, which are absorbed or extracted from the reactor effluent stream 12 by the first circulating fluid stream 18 in the first contact cooling zone 16 and/or from the first compressed product stream 56 by the second circulating fluid stream 58 in the second contact cooling zone 60. Drawing off the first drag stream 74 can also prevent fouling via build-up or condensation of heavy hydrocarbons within the heat exchanges zones such as, for example, in the first, second, third and/or indirect heat exchange zones 30, 44, 48 and 38, respectively. Reductions in fluid volume induced by drawing off or removing the first drag stream 74 from the processing scheme 10 can be compensated for by introducing fresh circulating fluid into the system via a first fresh circulating fluid stream 76.

The processing scheme 10 can still further involve compressing the second product stream 64 in a second compression zone 78 to produce a second compressed product stream 80 and contacting the second compressed product stream 80 with a third circulating fluid stream 82 in a third contact cooling zone 86 disposed within a third contact cooler 84. The second compressed product stream 80 contacts the third circulating fluid stream 82 in a countercurrent manner in the third contact cooling zone 86 wherein the second compressed product stream 80 is cooled to form a third product stream 88 and the third circulating fluid stream 82 is heated to form a third heated circulating fluid stream 90.

Similar to the first and second contact coolers 14 and 62, respectively, as described herein above, the third contact cooler 84 can include one or more contact cooling zones 86 in the form of a packed bed containing an inert packing material and/or a tray assembly. Advantageously, materials passing through the third contact cooler 84 from a second compressed product stream inlet 81 to a third product stream outlet 83 have a pressure drop of less than about 3.5 kPa (about 0.5 psi).

In accordance with certain embodiments, the second product stream 64 is compressed in the second compression zone 78 to form the second compressed product stream 80 having a delivery pressure in a range of about 1240 to about 1380 kPa gauge (about 180 to about 200 psig) and having a temperature in a range of about 120° C. to about 150° C. (about 250° F. to about 300° F.). Suitably, the second compressed product stream 80 is cooled via contact with the third circulating fluid stream 82 in the third contact cooling zone 86 to form the third product stream 88 having a temperature in a range of about 35° C. to about 55° C. (about 95° F. to about 130° F.). Further, the third circulating fluid stream 82 having a temperature in a range of about 20° C. to about 40° C. (about 70° F. to about 105° F.) is heated via contact with the second compressed product stream 80 in the third contact cooling zone 86 to form the third heated circulating fluid stream 90 having a temperature in a range of about 65° C. to about 95° C. (about 150° F. to about 200° F.).

Thermal energy can be recovered from the third heated circulating fluid stream 90 via indirect heat exchange with a second process stream 92 in a fourth heat exchange zone 94 wherein the third heated circulating fluid stream 90 is cooled to form a fourth cooled circulating fluid stream 96 and the second process stream 92 is treated to form a second treated process stream 98. In accordance with certain embodiments, the third heated circulating fluid stream 90 may be cooled to form the fourth cooled circulating fluid stream 96 having a temperature in a range of about 50° C. to about 65° C. (about 120° F. to about 150° F.).

In accordance with certain embodiments, thermal energy recovered from the third heated circulating fluid stream 90 and transferred via indirect heat exchange into the second treated process stream 98 can be used to supplement and/or replace other sources of thermal energy such as, for example, steam, used in associated fractionation units. For example, the second treated process stream 98 may be introduced into an associated deethanizer unit (not shown) to facilitate fractionation of a propane-containing feed or byproduct stream, such as via a reboiling process, into a purified propane-containing stream and a byproduct stream containing $C_2$– hydrocarbons. In practice, such purified propane-containing stream can be introduced or recycled into an associated propane-propylene (P-P) splitter unit (not shown) for further fractionation.

For example, it has been discovered that thermal energy recovered from the third heated circulating fluid stream 90 can be used to supplant up to about 50% of stream that is generally required to reboil a separation column in an associated deethanizer unit. In accordance with certain embodiments, about 10 about 40 MMBTU/hr of thermal energy can be recovered from the third heated circulating fluid stream 90. In practice, for a 350 KMTA propylene-producing system, about 20-35 MMBTU/hr of thermal energy recovered from the third heated circulating fluid stream 90 can be supplied to an associated deethanizer column reboiler.

The fourth cooled circulating fluid stream 96 can be subsequently cooled via indirect heat exchange in a fifth heat exchange zone 100 to form a fifth cooled circulating fluid stream 102. The fifth heat exchange zone 100 can include any suitable heat exchange unit such as known to those skilled in the art. In accordance with certain embodiments, the second heat exchange zone 100 can include an air cooler unit.

In practice, the fourth cooled circulating fluid stream 96 can be cooled via indirect heat exchange in the fifth heat exchange zone 100 to form the fifth cooled circulating fluid stream 102 having a temperature in a range of about 20° C. to about 55° C. (about 70° F. to about 130° F.). In accordance with certain embodiments, the fourth cooled circulating fluid stream 96 can be cooled via indirect heat exchange in the fifth heat exchange zone 100 to form the fifth cooled circulating fluid stream 102 having a temperature in a range of about 40° C. to about 50° C. (about 105° F. to about 125° F.).

The fifth cooled circulating fluid stream 102 can subsequently be separated to form the third circulating fluid stream 82 and a second drag stream 104. The second drag stream 104 is advantageously drawn off or removed from the processing scheme 10 to reduce or eliminate the build-up of heavy hydrocarbons such as, for example, $C_7$+ hydrocarbons and/or aromatic hydrocarbons such as, for example, benzene and toluene, which are absorbed or extracted from the second compressed product stream 80 by the third circulating fluid stream 82 in the third contact cooling zone 86. Drawing off the second drag stream 104 can also prevent fouling via build-up or condensation of heavy hydrocarbons within the heat exchange zones such as, for example, in the fourth and fifth heat exchange zone 94 and 100, respectively. Reductions in fluid volume induced by drawing off or removing the second drag stream 104 from the processing scheme 10 can be compensated for by introducing fresh circulating fluid into the system via a second fresh circulating fluid stream 106.

Thermal energy can additionally be recovered from the fifth cooled circulating fluid stream 102 via indirect heat exchange with a fourth process stream 108 in a sixth heat exchange zone 110 prior to separating the fifth cooled circulating fluid stream 102 into the third circulating fluid stream 82 and the second drag stream 104. In accordance with certain embodiments, thermal energy recovered from the fifth cooled circulating fluid stream 102 can be transferred to the fourth process stream 108 having a temperature in a range of about 20° C. to about 45° C. (about 70° F. to about 110° F.) to produce a fourth heated process stream 112 having a temperature in a range of about 32° C. to about 55° C. (about 90° F. to about 130° F.). In accordance with certain further embodiments, the fourth heated process stream 112 can be utilized to introduce heat into an associated thermal processing unit such as, for example, a propane-propylene (P-P) splitter unit (not shown).

The third product stream 88 can be subsequently dried and introduced into a cryogenic separation system (not shown) where it is cooled to form a partially condensed product stream. The partially condensed product stream is then directed to a separator wherein the partially condensed product stream is separated into the desired final product and by-product streams.

In accordance with certain embodiments a total of about 70 to about 120 MMBTU/hr of thermal energy can be recovered utilizing processing scheme 10.

The processing scheme 10 can further include one or more pumping zones to facilitate flow of the circulating fluid streams through the contact coolers. For example, the processing scheme 10 can include a first pumping zone 114 disposed between a first fresh circulating fluid stream inlet 116 and the first heat exchange zone 30. Additionally or alternatively, the processing scheme can include a second pumping zone 118 disposed between a second fresh circulating fluid stream inlet 120 and the fourth heat exchange zone 94. Each of the first and second pumping zones 114 and 118, respectively, can include, for example, a centrifugal pump for facilitating flow of circulating fluid through the processing scheme.

The processing scheme 10 can further include one or more heating zones to facilitate start-up of associated fractionation units. For example, the processing scheme 10 can include a first heating zone 122 disposed between the first pumping zone 114 and the first heat exchange zone 30 wherein the first portion 70 of the combined heated circulating fluid stream 68 is heated to a select temperature in the first heating zone prior entering the first heat exchange. Additionally or alternatively, the processing scheme 10 can include a second heating zone 124 disposed between the second pumping zone 118 and the fourth heat exchange zone 94 wherein the third heated circulating fluid stream 90 is heated to a select temperature in the second heating zone 124 prior to entering the fourth heat exchange zone. In accordance with certain embodiments, the first and/or the second heating zones 122 and 124, respectively, can include a steam heater.

Figure 2:
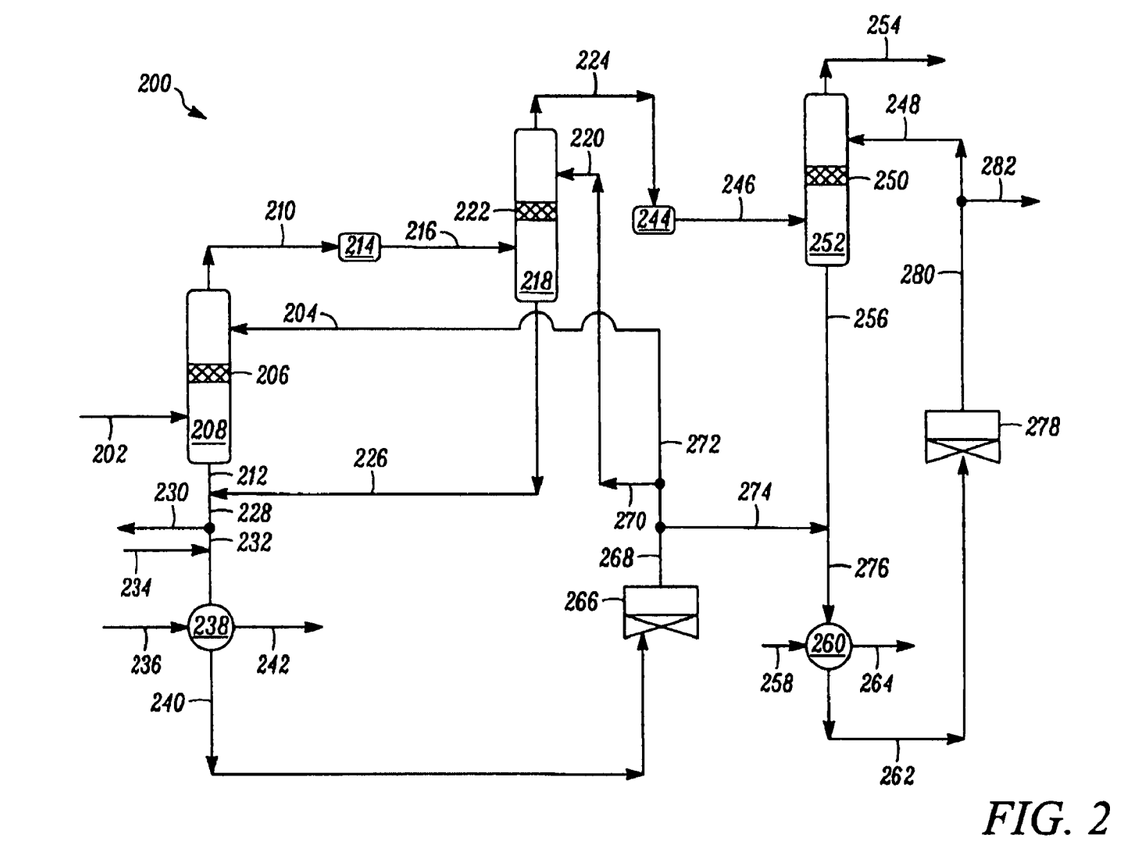
FIG. 2 is a simplified schematic diagram of a process for recovering thermal energy from a dehydrogenation reactor effluent stream in accordance with another embodiment.

In accordance with another embodiment, as illustrated FIG. 2, a processing scheme and system, generally designated by reference numeral 200, for recovering thermal energy from a reactor effluent stream 202 resulting from dehydrogenation of a dehydrogenatable hydrocarbon involves contacting the reactor effluent stream 202 with a first circulating fluid stream 204 in a first contact cooling zone 206 disposed within a first contact cooler 208. The reactor effluent stream 202 contacts the first circulating fluid stream 204 in a countercurrent manner in the first contact cooling zone 206 wherein the reactor effluent stream 202 is cooled to form a first product stream 210 and the first circulating fluid stream 204 is heated to form a first heated circulating fluid stream 212.

The reactor effluent stream 202, the first circulating fluid stream 204, the first product stream 210 and the first heated circulating fluid stream 212 can have temperature and/or pressure profiles similar to the temperature and/or pressure profiles described above in conjunction with the reactor effluent stream 12, the first circulating fluid stream 18, the first product stream 20, and the first heated circulating fluid stream 22, respectively, as illustrated in FIG. 1.

The first product stream 210 can be compressed in first compression zone 214 to form a first compressed product stream 216. The first compressed product stream 216 can be subsequently cooled in a second contact cooler 218. More particularly, the first compressed product stream 216 is cooled by contacting a second circulating fluid stream 220 in a countercurrent manner in a second contact cooling zone 222 disposed within the second contact cooler 218 to form a second product stream 224. Further, the second circulating fluid stream 220 is heated via contact with the first compressed product stream 216 in the second cooling zone 222 to form a second heated circulating stream 226.

The first compressed product stream 216, the second circulating fluid stream 220, the second product stream 224 and the second heated circulating fluid stream 226 can have temperature and/or pressure profiles similar to the temperature and/or pressure profiles described above in conjunction with the first compressed product stream 56, the second circulating fluid stream 58, the second product stream 64 and the second heated circulating fluid stream 66, respectively, and illustrated in FIG. 1.

The first heated circulating fluid stream 212 and the second heated circulating fluid stream 226 can be combined to form a first combined heated circulating fluid stream 228. The first combined heated circulating fluid stream 228 can then be separated into a first drag stream 230 and a heated recycle fluid stream 232.

The first drag stream 230 is advantageously drawn off or removed from the processing scheme 200 to reduce or eliminate the build-up of heavy hydrocarbons such as, for example, $C_7+$ hydrocarbons and/or aromatic hydrocarbons such as, for example, benzene and toluene, which are absorbed or extracted from the reactor effluent stream 202 by the first circulating fluid stream 204 in the first contact cooling zone 206 and/or from the first compressed product stream 216 by the second circulating fluid stream 220 in the second contact cooling zone 222. Drawing off the first drag stream 230 can also prevent fouling via build-up or condensation of heavy hydrocarbons within the processing scheme 200. Reductions in fluid volume induced by drawing off or removing the first drag stream 230 from the processing scheme 200 can be compensated for by introducing fresh circulating fluid into the processing scheme 200 via a first fresh circulating fluid stream 234.

Thermal energy can be recovered from the heated recycle fluid stream 232 via indirect heat exchange with a first process stream 236 in a first heat exchange zone 238. In practice, the heated recycle fluid stream 232 is cooled via indirect heat exchange with the first process stream 236 to form a first cooled circulating fluid stream 240 and the first process stream 236 is heated via indirect heat exchange with the heated recycle fluid stream 232 to form a first heated process stream 242.

The heated recycle fluid stream 232, the first process stream 236, the first cooled circulating fluid stream 240 and the first heated process stream 242 can have temperature profiles similar to the temperature profiles described above in conjunction with the first heated circulating fluid stream 22, the first process stream 28, the first cooled circulating fluid stream 32, and the first heated process stream 34, respectively, and illustrated in FIG. 1.

The thermal energy recovered from the heated recycle fluid stream 232 and transferred via indirect heat exchange into to the first heated process stream 242 can be used to supplement and/replace other source of thermal energy such as, for example, steam, used in associated fractionation units. In accordance with certain embodiments, the thermal energy recovered from the heated recycle fluid stream can be used to supplant up to about 50% of the steam that is generally required to reboil a separation column in an associated depropanizer unit (not shown). In accordance with certain further embodiments, about 10 to about 40 MMBTU/hr of thermal energy may be recovered from the heated recycle fluid stream 232 in the first heat exchange zone 238.

The processing scheme 200 can further involve compressing the second product stream 224 in a second compression zone 244 to produce a second compressed product stream 246 and contacting the second compressed product stream 246 with a third circulating fluid stream 248 in a third contact cooling zone 250 disposed within a third contact cooler 252. In practice, the second compress product stream 246 contacts the third circulating fluid stream 248 in a countercurrent manner in the third contact cooling zone 250 wherein the second compressed product stream 246 is cooled to produce a third product stream 254 and the third circulating fluid stream 248 is heated to form a third heated circulating fluid stream 256.

The second compressed product stream 246, the third circulating fluid stream 248, the third product stream 254 and the third heated circulating fluid stream 256 can have temperature and/or pressure profiles similar to the temperature and/or pressure profiles described above in conjunction with the second compressed product stream 80, the third circulating fluid stream 82, the third product stream 88, and the third heated circulating fluid stream 90, respectively, and illustrated in FIG. 1.

The third product stream 254 can be subsequently dried and introduced into a cryogenic separation system (not shown) where it is cooled to form a partially condensed product stream. The partially condensed product stream is then directed to a separator wherein the partially condensed product stream is separated into the desired final product and by-product streams.

Generally, the first contact cooler 208, the second contact cooler 218, and the third contact cooler 252 can be constructed and/or configured in a manner such as described above in conjunction with the first contact cooler 14, the second contact cooler 62, and the third contact cooler 84, respectively, and illustrated in FIG. 1. Advantageously, materials passing through the first, second and third, contact coolers 208, 218 and 252, respectively, from an effluent or product stream inlet to a product stream outlet have a pressure drop of less than about 3.5 kPa (about 0.5 psi).

Thermal energy can be recovered from the third heated circulating fluid stream 256 via indirect heat exchange with a second process stream 258 in a second heat exchange zone 260. In practice, the third heated circulating fluid stream 256 is cooled via indirect heat exchange with the second process stream 258 to form a second cooled circulating fluid stream 262 and the second process stream 258 is heated via indirect heat exchange with the third heated circulating fluid stream 256 to form a first treated process stream 264.

The second process stream 258 and the second cooled circulating fluid stream 262 can have temperature profiles similar to the temperature profiles described above in conjunction with the second process stream 92 and the fourth cooled circulating fluid stream 96, respectively, and illustrated in FIG. 1.

The thermal energy recovered from the third heated circulating fluid stream 256 and transferred via indirect heat exchange into the first treated process stream 264 can be used to supplement and/replace other sources of thermal energy such as, for example, steam, used in associated fractionation units. In accordance with certain embodiments, the thermal energy recovered from the heated recycle fluid stream can be used to supplant up to about 50% of the steam that is generally required to reboil a separation column in an associated deethanizer unit (not shown). In accordance with certain further embodiments, about 10 to about 40 MMBTU/hr of thermal energy may be recovered from the third heated circulating fluid stream 256 in the second heat exchange zone 260.

The processing scheme 200 can still further involve cooling the first cooled circulating fluid stream 240 via indirect heat exchange in a third heat exchange zone 266 to form a third cooled circulating fluid stream 268. The third cooled circulating fluid stream 268 can have temperature profile similar to the temperature profile described above in conjunction with the third cooled circulating fluid stream 46 and illustrated in FIG. 1.

The third cooled circulating fluid stream 268 can be subsequently separated into a first portion 270, a second portion 272 and a third portion 274. The first portion 270 of the third cooled circulating fluid stream 268 can be recycled to the second contact cooler 218 to provide the second circulating fluid stream 220. The second portion 272 of the third cooled circulating fluid stream 268 can be recycle to the first contact cooler 208 to provide the first circulating fluid stream 204.

The third portion 274 of the third cooled circulating fluid stream 268 can be combined with the third heated circulating fluid stream 256 to form a second combined hearted circulating fluid stream 276. Thermal energy can be recovered from the second combined heated circulating fluid stream 276 via indirect heat exchange with the second process stream 258 in the second heat exchange zone 260.

The processing scheme 200 can additionally involve cooling the second cooled circulating fluid stream 262 via indirect heat exchange in a fourth heat exchange zone 278 to form a fourth cooled circulating fluid stream 280. The fourth cooled circulating fluid stream 280 can have a temperature profile similar to the temperature profile described above in conjunction with the fifth cooled circulating fluid stream 102 and illustrated in FIG. 1.

The fourth cooled circulating fluid stream 280 can be subsequently separated to produce a second drag stream 282 and to provide the third circulating fluid stream 248. Reductions in fluid volume induced by drawing off or removing the second drag stream 282 can be compensated for by introducing fresh circulating fluid into the system via the first fresh circulating fluid stream 234 and combining the third portion 274 of the third cooled circulating fluid stream 268 with the third heated circulating fluid stream 256.

In accordance with certain embodiments, about 70 to about 120 MMBTU/hr of thermal energy may be recovered utilizing processing scheme 200.

Embodiments, such as described above, desirably provide or result in improved processing of dehydrogenation reactor effluent streams to produce an increased relative yield of olefins and which processing is desirably more effective and/or efficient than heretofore reasonably possible via conventional catalytic dehydrogenation processing and associated product separation processes.

More specifically, such embodiments, through cooling of dehydrogenation reactor effluent streams via direct contact with a circulating fluid stream, can improve processing economics. For example, such processing can desirable minimize system fouling by heavy hydrocarbons and reduce differential pressure losses during cooling and recovery processes. Further, thermal energy recovered from circulating fluid streams can be used to, at least in part, supplement and/or supplant thermal energy inputs from sources external to the overall dehydrogenation and product recovery process such as, for example, steam inputs into associated fractionation units, thus resulting in improved process economics.

The invention illustratively disclosed herein suitably may be practiced in the absence of any element, part, step, component or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A process for recovering thermal energy from a reactor effluent stream resulting from dehydrogenation of a dehydrogenatable hydrocarbon, the process comprising:
   contacting the reactor effluent stream with a first circulating fluid stream in a first contact cooling zone wherein the reactor effluent stream is cooled to form a first product stream and the first circulating fluid stream is heated to form a first heated circulating fluid stream;
   recovering thermal energy from the first heated circulating fluid stream via indirect heat exchange with a first process stream in a first heat exchange zone wherein the first heated circulating fluid stream is cooled to form a first cooled circulating fluid stream and the first process stream is heated to form a heated first process stream;
   compressing the first product stream in a first compression zone to produce a first compressed product stream; and
   contacting the first compressed product stream with a second circulating fluid stream in a second contact cooling zone wherein the first compressed product stream is cooled to form a second product stream and the second circulating fluid stream is heated to form a second heated circulating fluid stream.

2. The process of claim 1 wherein about 10 to about 40 MMBTU/hr of thermal energy is recovered from the first heated circulating fluid stream.

3. The process of claim 1 additionally comprising:
   cooling at least a first portion of the first cooled circulating stream to produce the first circulating fluid stream.

4. The process of claim 1 wherein the dehydrogenatable hydrocarbon comprises propane.

5. The process of claim 4 additionally comprising:
   recovering thermal energy from the first cooled circulating fluid stream via indirect heat exchange with at least one propane-containing stream wherein the first cooled circulating fluid stream is cooled to form a second cooled circulating fluid.

6. The process of claim 5 additionally comprising:
   cooling the second cooled circulating fluid stream via indirect heat exchange in a second heat exchange zone to form a third cooled circulating fluid stream.

7. The process of claim 6 additionally comprising:
   recovering thermal energy from the third cooled circulating fluid stream via indirect heat exchange in a third heat exchange zone wherein the third cooled circulating fluid stream is cooled to produce the first circulating fluid stream.

8. The process of claim 1 additionally comprising:
   combining the second heated circulating fluid stream with the first heated circulating fluid stream to form a combined heated circulating fluid stream; and
   cooling a first portion of the combined heated circulating fluid stream via indirect heat exchange in the first heat exchange zone.

9. The process of claim 8 additionally comprising:
drawing off a second portion of the combined heated circulating fluid stream to form a first drag stream.

10. The process of claim 1 additionally comprising:
compressing the second product stream in a second compression zone to produce a second compressed product stream;
contacting the second compressed product stream with a third circulating fluid stream in a third contact cooling zone wherein the second compressed product stream is cooled to form a third product stream and the third circulating fluid stream is heated to form a third heated circulating fluid stream; and
recovering thermal energy from the third heated circulating fluid stream via indirect heat exchange with a second process stream in a fourth heat exchange zone wherein the third heated circulating fluid stream is cooled to form a fourth cooled circulating fluid stream.

11. The process of claim 10 additionally comprising:
cooling the fourth cooled circulating fluid stream via indirect heat exchange in a fifth heat exchange zone to form a fifth cooled circulating fluid stream; and
separating the fifth cooled circulating fluid stream to form the third circulating fluid stream and a second drag stream.

12. The process of claim 11 additionally comprises:
recovering thermal energy from the fifth cooled circulating fluid stream via indirect heat exchange with a fourth process stream in a sixth heat exchange zone prior to separating the fifth cooled liquid stream.

13. A process for recovering thermal energy from a reactor effluent stream resulting from the dehydrogenation of a dehydrogenatable hydrocarbon, the process comprising:
contacting the reactor effluent stream with a first circulating fluid stream in a first contact cooling zone wherein the reactor effluent stream is cooled to form a first product stream and the first circulating fluid stream is heated to form a first heated circulating fluid stream;
compressing the first product stream in a first compression zone to produce a first compressed product stream;
contacting the first compressed product stream with a second circulating fluid stream in a second contact cooling zone wherein the first compressed product stream is cooled to form a second product stream and the second circulating fluid stream is heated to form a second heated circulating fluid stream;
combining the first heated circulating fluid stream and the second heated circulating fluid stream to form a first combined heated circulating fluid stream;
separating the first combined heated circulating fluid stream into a first drag stream and a heated recycle fluid stream; and
recovering thermal energy from the heated recycle fluid stream via indirect heat exchange with a first process stream in a first heat exchange zone wherein the heated recycle fluid stream is cooled to form a first cooled circulating fluid stream and the first process stream is heated to form a first heated process stream.

14. The process of claim 13 wherein about 10 to about 40 MMBTU/hr of thermal energy is recovered from the heated recycle fluid stream.

15. The process of claim 13 additionally comprising:
compressing the second product stream in a second compression zone to produce a second compressed product stream;
contacting the second compressed product stream with a third circulating fluid stream in a third contact cooling zone wherein the second compressed product stream is cooled to form a third product stream and the third circulating fluid stream is heated to form a third heated circulating fluid stream;
recovering thermal energy from the third heated circulating fluid stream via indirect heat exchange with a second process stream in a second heat exchange zone to produce a first treated process stream and to form a second cooled circulating fluid stream.

16. The process of claim 15 additionally comprising:
cooling the first cooled circulating fluid stream via indirect heat exchange in a third heat exchange zone to form a third cooled circulating fluid stream;
recycling a first portion of the third cooled circulating fluid stream to the second contact cooling zone to provide the second circulating fluid stream;
recycling a second portion of the third cooled circulating fluid stream to the first contact cooling zone to provide the first circulating fluid stream; and
combining a third portion of the third cooled circulating fluid stream with the third heated circulating fluid stream to form a second combined circulating fluid stream; and
recovering thermal energy from the second combined circulating fluid stream via indirect heat exchange with the second process stream in the second heat exchange zone.

17. The process of claim 15 additionally comprising:
cooling the second cooled circulating fluid stream via indirect heat exchange in a fourth heat exchange zone to form a fourth cooled circulating fluid stream; and
separating the fourth cooled circulating fluid stream to produce a second drag stream and to provide the third circulating fluid stream.

18. The process of claim 15 wherein the first circulating fluid stream, the second circulating fluid stream and the third circulating fluid stream comprises a liquid selected from the group consisting of light cycle oil, low-sulfur diesel, kerosene and combinations thereof.

19. The process of claim 15 wherein a total of about 70 to about 120 MMBTU/hr of thermal energy is recovered from the reactor effluent stream.

* * * * *